United States Patent [19]

Nafissi-Varchei

[11] 4,006,242
[45] Feb. 1, 1977

[54] CERTAIN BENZOTHIAZOLES USED IN THE TREATMENT OF HELMINTHIASIS

[75] Inventor: Mohammad Mehdi Nafissi-Varchei, North Caldwell, N.J.

[73] Assignee: Schering Corporation, Kenilworth, N.J.

[22] Filed: Apr. 25, 1975

[21] Appl. No.: 571,875

Related U.S. Application Data

[63] Continuation-in-part of Ser. No. 381,112, July 18, 1973, abandoned.

[30] Foreign Application Priority Data

July 8, 1974 Switzerland ............... 9468/74

[52] U.S. Cl. ............................................. 424/270
[51] Int. Cl.² .................. A01N 9/20; A61K 31/425

[58] Field of Search ..................... 424/270

[56] References Cited
UNITED STATES PATENTS

| | | | |
|---|---|---|---|
| 3,555,157 | 1/1971 | Lindemann | 424/270 |
| 3,725,428 | 4/1973 | Janiak | 424/270 X |

*Primary Examiner*—Leonard Schenkman
*Attorney, Agent, or Firm*—Bruce M. Eisen; Stephen B. Coan

[57] ABSTRACT

A novel treatment of helminthiasis is provided by means of the administration of specified benzothiazoles.

6 Claims, No Drawings

CERTAIN BENZOTHIAZOLES USED IN THE TREATMENT OF HELMINTHIASIS

This application is a continuation-in-part of my co-pending application Ser. No. 381,112 filed July 18, 1973, now abandoned.

This invention relates to the use of a small class of carbamate esters of benzothiazoles which are particularly effective anthelmitic agents, and to pharmaceutical formulations, especially oral dosage forms, containing the same.

These benzothiazoles have the general formula:

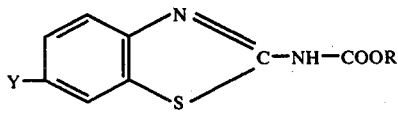

wherein Y is ethoxy or n-propoxy and R is methyl or ethyl.

Thus, this formula includes the following four compounds:

Ethyl-6-ethoxybenzothiazole-2-carbamate;
Ethyl-6-n-propoxybenzothiazole-2-carbamate;
Methyl-6-ethoxybenzothiazole-2-carbamate; and
Methyl-6-n-propoxybenzothiazole-2-carbamate.

The preferred compound for use in the invention is methyl-6-n-propoxybenzothiazole-2-carbamate, which is a novel substance.

Compounds of the above formula are generically known in the art; as for example U.S. Pat. Nos. 3,555,157 and 3,725,428 and the Journal of the Pharmaceutical Society of Japan, Vol. 69, pgs. 398–400 (1949). The prior art describes the use of such benzothiazoles as horticultural microbiocides, and in particular fungicides, but their anthelmintic activity had apparently not been known. While the prior art does teach the anthelmintic activity of corresponding benzimidazoles, e.g. oxibendazole, such general correspondence neither is recognized in the art nor does in fact exist. For example, mebendazole (Y is benzoyl, R is methyl) is a leading and highly effective anthelmintic. However, its benzothiazole analog has little or no anthelmintic activity.

The compounds of this invention may be prepared according to known processes, e.g. as described in the above references. Five applicable methods are described below (in each Y and R are as above defined)

1.

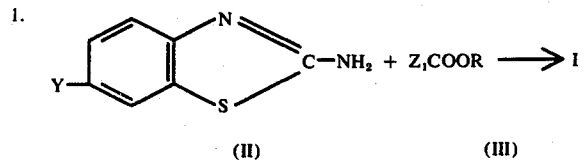

wherein $Z_1$ is a reactive labile group such as halogen. The process is preferably carried out in a suitable solvent such as pyridine at a reduced temperature, i.e. between 0° C and room temperature. The formate is added slowly to amine-containing solvent with stirring. The desired carbamate is then isolated according to techniques well known in the art. Purification can be effected by recrystallization in the usual manner. Although pyridine is the preferred solvent for this reaction, other solvents such as acetonitrile and triethylamine and mixtures of acetonitrile and pyridine may also be used.

2.

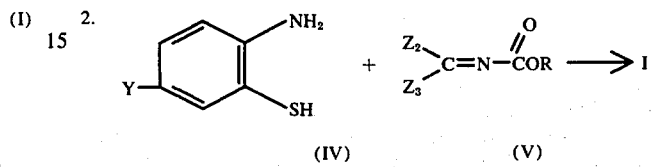

wherein $Z_2$ and $Z_3$ are reactive labile groups such as $-SCH_3$, $-OCH_3$ or $-N(CH_3)_2$.

The reaction is preferably carried out by stirring and heating the reactants at reflux temperature in a suitable solvent such as ethanol, keeping the reaction mixture under an inert atmosphere, preferably nitrogen.

3.

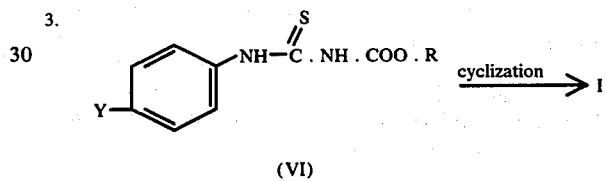

Also this process is carried out using standard techniques. One preferred method comprises heating the thiourea compound in a suitable solvent such as chloroform at reflux temperature in the presence of bromine. Instead of heating, one may also irradiate the reaction mixture. The isolation of the product is also performed according to standard procedures. The mixture is brought to room temperature, washed with aqueous $Na_2CO_3$, and aqueous NaCl and dried over sodium sulfate. The solvent is removed by evaporation to yield the desired product. The intramolecular cyclization may also be accomplished by adding an aqueous solution of potassium ferricyanide to a stirred and moderately heated mixture of the thiourea compound, sodium hydroxide and water. After the addition of potassium ferricyanide is completed, potassium carbonate is added and the stirring is continued. The reaction mixture is then extracted with a suitable solvent, preferably chloroform. The extracts are dried over sodium sulfate and the solvent is evaporated to yield the desired product.

4.

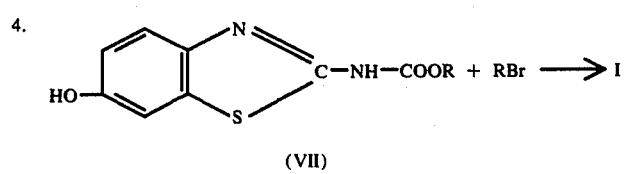

The etherification is preferably carried out by heating a mixture of the hydroxybenzothiazole-2-carbamate, anhydrous potassium carbonate, n-propylbromide and a suitable solvent, e.g. acetone, at reflux temperature. The solvent is then removed by distillation, the residue taken into water and filtered. The pure product is obtained by recrystallization from ethanol.

5. A further process comprises reacting a benzothiolzole-2-isocyanate of the general formula

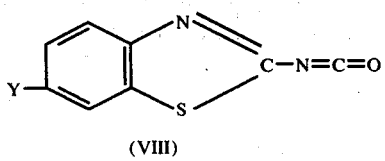

(VIII)

or a reactive derivative thereof with methanol or ethanol. The reaction is preferably carried out by stirring a mixture of the anhydrous reactants in a solvent such as an excess of alkanol, or benzene, at room temperature. The preferred reactive derivatives of the compounds of formula X are those wherein the group $-N=C=O$ is replaced by the grouping

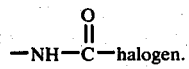

The appropriate starting compounds in the above processes 1 to 4 may be obtained by techniques well known in the art. The 2-amino-benzothiazoles may be obtained by cyclizing the appropriate aniline with an alkali metal isothiocyanate (MSCN) and cupric chloride in an acidic solvent such as acetic acid.

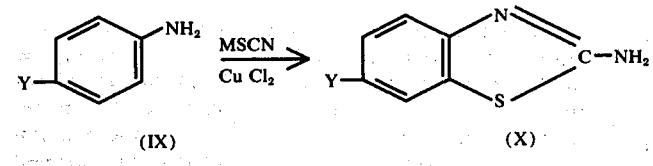

The following examples serve to exemplify the above described processes. Examples 1 and 2 illustrate the preferred process and Examples 3 to 6 illustrate alternative processes.

EXAMPLE 1

Preparation of methyl-6-n-propyloxybenzothiazole-2-carbamate

To a stirring solution of 24.45 g. of 2-amino-6-n-propyloxybenzothiazole-hydrochloride in 100 ml of pyridine maintained at 0° C. by an ice bath, is slowly added 9.45 g. of methyl chloroformate. After the addition is completed the mixture is allowed to warm up to room temperature. It is then poured on 300 g. of ice water. A solid is formed which is isolated by filtration and crystallized from ethanol yield 20g m.p. 178°–180° C.

EXAMPLE 2

Preparation of ethyl-6-n-propoxybenzothiazole-2-carbamate

To a chilled solution of 10.4 g. 2-amino-6-n-propoxybenzothiazole in 50 ml dry pyridine is dropwise added 6 g. ethyl chloroformate with stirring. The mixture is then allowed to stand at room temperature for 8 hrs. It is poured in 200 g. of ice water and stirred for 30 mins. The white solid product is separated by filtration and dried. Crystallization from ethanol gave 12 g. of the product. m.p. 175°–177° C.

EXAMPLE 3

Preparation of methyl-6-n-propoxybenzothiazole-2-carbamate

In a round bottom 1 liter flask equipped with a reflux condenser, a magnetic stirrer and a heating mantle is placed 45.75 g. of 2-mercapto-4-propoxyaniline; 48.25 g. of methyl-N-[di(methylthio)-methylene] carbamate, and 250 ml absolute ethanol. This mixture is heated to boiling under an inert atmosphere of nitrogen for 12 hrs. It is then chilled and the white crystalline solid which is formed is isolated by filtration, washed with cold ethanol and dried. m.p. 178°–180° C.

EXAMPLE 4

Preparation of methyl-6-n-propoxybenzothiazole-2-carbamate

A solution of 28.2 g. 1-carbomethoxy-3-(n-propoxyphenyl) thiourea and 16 g. bromine in 700 ml of chloroform is irradiated in a quartz vessel by a 450 W medium pressure mercury lamp until the color of bromine disappears. The reaction mixture is then washed with a 5% aqueous sodium hydroxide solution, dried over anhydrous sodium sulfite, and the organic solvent is evaporated to give a solid which is crystallized from ethanol and yields 26 g. of the desired compound. m.p. 178°–180° C.

EXAMPLE 5

Preparation of methyl-6-n-propoxybenzothiazole-2-carbamate

To a stirred suspension of 2.2 g. 1-carbomethoxy-3-(p-n-propoxyphenyl) thiourea in a solution of 2.42 g. sodium hydroxide in 35 ml of water, in an erlenmeyer flask at 64° (by water bath) is added a solution of 8.8 g. potassium ferricyanide in 20 ml water. The stirring is continued for 2 additional hrs. Potassium carbonate, 6 g. is then added to this reaction mixture and stirring is continued for another 2 hr. period. It is then extracted by 2 × 50 ml chloroform. The chloroform extracts are dried over anhydrous Na₂SO₄ and the solvent is removed by evaporation to give 2 g. of the product. m.p. 178°–180° C.

EXAMPLE 6

Preparation of methyl-6-n-propoxybenzothiazole-2-carbamate

A mixture of 11.5 g. anhydrous 6-n-propoxybenzothiazole-2-isocyanate, 5 g. anhydrous methanol and 50 ml benzene is stirred at room temperature for 4–5 hours, is then poured into ice water and stirred for 30 minutes. The white solid product is isolated by filtration and recrystallized from ethanol. m.p. 178°–180° C.

By using the appropriate starting compounds in the above processes one may analogously prepare methyl-6-ethoxybenzothiazole-2-carbamate and ethyl-6-ethoxybenzothiazole-2-carbamate.

The compounds of this invention are useful in treating humans and animals suffering from helminthiasis, i.e. an infestation of the gastrointestinal tract with parasitic worms, by administering to the host animal a therapeutic amount thereof. These compounds combine a high degree of anthelmintic activity with low host toxicity, i.e. a high therapeutic index. Moreover, the anthelmintic activity is broad spectrum. They are effective against the four most prevalent nematodes known to infest mammals, i.e. the compounds exhibit an effective anthelmintic effect against worm types such as *S. Obvalata* (pinworm), Ascaridae (roundworm), Ancylostomatidal (hookworm) and Trichuris (whipworm). For example, in the horse the preferred compound of this invention exhibits potent activity against large strongylest, e.g. *S. vulgaris*, *S. edentatus* and *S. equinus*; small strongyles, *Oxyuris equi* and *P. equorum*.

The anthelmintic activity of the subject compounds is evaluated according to standard techniques such as the Modified McMaster Egg Counting Technique as described by H. B. Whitlock and H. McL. Gordon: J. Council Scientific Industrial Research (Australia) 12: p. 50, 1939 and H. B. Whitlock: J. Council Scientific Research (Australia) 21: p. 177, 1948. From these and similar tests anthelmintic efficiency is assessed by determining the number of eggs in faeces passed on the days following treatment with the compounds.

From such tests it is determined that the compounds of this invention exhibit significant anthelmintic effects when administered to an infested host (e.g. a horse) in the dose range of 30–100 mg/kg per day. Single or multiple dosing is contemplated using standard art techniques. The compounds of this invention are preferably orally administered in the standard oral dosage forms such as tablets, boluses, capsules, elixirs, drenches or as feed additives. In addition, the compounds may also be used as injectible anthelmintic preparations. For this purpose the active ingredients are admixed with suitable sterile carriers such as sterile water and isotonic saline solution.

The following examples illustrate typical formulations:

| A: Tablet formulation | Grams per 1000 tablets |
|---|---|
| Methyl-6-n-propoxybenzothiazole-2-carbamate | 200.0 |
| Lactose | 90.0 |
| Dicalcium phosphate, hydrous | 122.5 |
| Polyvinylpyrolidone | 25.0 |
| Polyethylene glycol 1500 | 7.5 |
| Corn Starch | 50.0 |
| Magnesium Stearate | 5.0 |
| | 500.0 |

Mix the carbamate, the lactose and the dicalcium phosphate. Dissolve the polyethylene glycol 1500 and the polyvinylpyrolidone in approximately 20 ml of water. Granulate the powder blend with the water solution, adding additional water if necessary, to produce a damp mass. Pass the wet granulation through a 12 mesh screen; spread on trays and air dry at 35° C. Blend the dry granulates with the starch and the magnesium stearate. Compress into 500 mg. tablets.

| B: Capsule formulation | Grams per 1000 capsules |
|---|---|
| Methyl-6-n-propoxybenzothiazole-2-carbamate | 200.0 |
| Lactose | 198.0 |
| Magnesium Stearate | 2.0 |
| | 400.0 |

Blend the ingredients and fill into hard gelatine capsules.

| C: Elixir formulation | Per 1000 ml |
|---|---|
| Methyl-6-ethoxybenzothiazole-2-carbamate | 40 g. |
| Sugar | 500 g. |
| Glycerin | 200 g. |
| Compound Orange Spirit | 10 ml |
| Alcohol | 100 ml |
| Amaranth | 0.1 ml |
| Sodium Citrate | 10 g. |
| Water to total | 1000 ml |

What is claimed is:
1. A method of treating helminthiasis in mammals which comprises administering to a mammal suffering therefrom an anthelmintically effective quantity of a benzothiazole of the formula

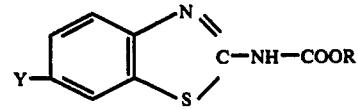

wherein Y is ethoxy or n-propoxy and R is methyl or ethyl.

2. A method according to clam 1 wherein R is methyl.

3. A method according to claim 1 wherein R is ethyl.

4. A method according to claim 1 wherein Y is n-propoxy.

5. A method according to claim 4 wherein R is methyl.

6. A method according to claim 1 wherein said administering is effected orally.

* * * * *